United States Patent [19]

Sitrin

[11] Patent Number: 4,882,313
[45] Date of Patent: Nov. 21, 1989

[54] CARBOXAMIDE DERIVATIVES OF GLYCOPEPTIDES

[75] Inventor: Robert D. Sitrin, Lafayette Hill, Pa.

[73] Assignee: SmithKline Beckman Corporation, Philadelphia, Pa.

[21] Appl. No.: 80,025

[22] Filed: Jul. 31, 1987

[51] Int. Cl.$^4$ .......... A61K 7/02; C07K 9/00; C07K 7/50
[52] U.S. Cl. .......... 514/8; 514/9; 530/317; 530/322; 426/635
[58] Field of Search .......... 530/317, 322; 514/8, 514/9; 426/635

[56] References Cited

U.S. PATENT DOCUMENTS

| | | | |
|---|---|---|---|
| 3,783,483 | 3/1973 | Nishida et al. | 424/118 |
| 3,803,306 | 4/1974 | Kunstmann et al. | 424/118 |
| 4,083,964 | 4/1978 | Michel et al. | 424/118 |
| 4,378,348 | 12/1975 | Raun | 424/118 |
| 4,497,802 | 2/1985 | Debono | 260/112.5 R |
| 4,521,335 | 6/1985 | Chan et al. | 260/112.5 R |
| 4,537,770 | 8/1985 | Michel et al. | 424/118 |
| 4,552,701 | 1/1985 | Nagarajan et al. | 260/112.5 R |

FOREIGN PATENT DOCUMENTS 8656598 10/1986 Australia .
218099A 9/1985 European Pat. Off. .
0182157 5/1986 European Pat. Off. .

OTHER PUBLICATIONS

Williams et al., Topics in Antibiotic Chemistry, vol. 5, pp. 119–158 (1980).
Malabarba et al., J. of Antibiotics, vol. 37, No. 9, pp. 988–999 (1984).
Barna et al., J. of Antibiotics, vol. 37, No. 10, pp. 1204–1208 (1984).
Jeffs et al., J. Org. Chem., vol. 50, pp. 1726–1731 (1984).

*Primary Examiner*—Lester L. Lee
*Assistant Examiner*—Christina Chan
*Attorney, Agent, or Firm*—Linda E. Hall; Janice E. Williams; Alan D. Lourie

[57] ABSTRACT

Carboxamide derivatives of glcopeptide antibiotics and their salts are useful for treating or preventing infection in an animal by gram-positive bacteria and also increase feed-utilization efficiency, promote growth in domestic animals and increase propionate production in lactating ruminants.

18 Claims, No Drawings

CARBOXAMIDE DERIVATIVES OF GLYCOPEPTIDES

FIELD OF THE INVENTION

This invention relates to carboxamide derivatives of glycopeptide antibiotics.

BACKGROUND OF THE INVENTION

The vancomycin/ristocetin class of glycopeptide antibiotics are amorphous, amphoteric, strongly laevorotatory compounds of relatively high molecular weight. Structurally, they comprise a heptapeptide aglycone core having phenolic amino acids and, usually, one or more peripheral carbohydrate moieties. See, Williams et al., Topics in Antibiotic Chemistry, Volume 5, pages 119–158. Known members of this class include vancomycin (McCormick et al., U.S. Pat. No. 3,067,099), ristocetin (Philip et al., U.S. Pat. No. 2,990,329), A35512 (Michel et al., U.S. Pat. No. 4,083,964), avoparcin (Kunstmann et al., U.S. Pat. No. 3,338,786 and Debono, U.S. Pat. No. 4,322,343), teicoplanin (Bardone et al., J. Antibiot., Volume 31, page 170, 1978), actaplanin (Raun, U.S. Pat. No. 3,816,618, Boeck et al., U.S. Pat. No. 4,537,715), AAD-216 ("ardacin") (Bowie et al., U.S. Pat. No. 4,548,974), A477 (Raun et al., U.S. Pat. No. 3,928,571), OA7653 (Nishida et al., U.S. Pat. No. 4,378,348), AM 374 (Kunstmann et al., U.S. Pat. No. 3,803,306), K288 (J. Antibiotics, Series A, Volume 14, page 141 (1961), also known as actinoidin), teichomycin (Borghi et al., U.S. Pat. No. 4,542,018, Malabarba et al., The Journal of Antibiotics, Vol. XXXVII, No. 9, p. 988–999, Barna et al., The Journal of Antibiotics, Vol. XXXII, No. 9, p. 1204–1208), desvancosaminyl and des(vancosaminyl-O-glucosyl) glycopeptides (Nagarajan, U.S. Pat. No. 4,552,701), AAJ-271, (Carr et al. copending application Ser. No. 892,027 now abandoned incorporated herein by reference), A 33512B (U.S. Pat. No. 4,029,769), A 41030 factors a-g (U.S. Pat. No. 770), AAD-609 (Ser. No. 781,422 now U.S. Pat. No. 4,694,069) and CWI-785 (copending applications Ser. Nos. 891,931, now U.S. Pat. No. 4,742,045 and 892,174, now abandoned, incorporated by reference herein).

The glycopeptide antibiotics exhibit antibacterial activity, some having therapeutic uses against gram-positive organisms including methicillin-resistant strains. These strains currently cannot be treated with β-lactam antibiotics, including the newer β-lactamase-resistant cephalosporins. Infections by these pathogens is a serious problem. For example the compounds of this invention may be used to treat staphylococcal endocarditis, osteomyelitis, pneumonia, septicemia, soft tissue infection, staphylococcal enterocolitis and antibiotic-associated pseudomembranous colitis produced by *C. difficile*. They may also be used for prophylaxis for hip and heart surgery, prophylaxis against bacterial endocarditis and *S. aureus* infections in hemodialysis patients.

Many glycopeptides have also been demonstrated to increase animal feed utilization efficiency and, therefore, to be useful to promote animal growth, to improve milk production in ruminants and to treat and to prevent ketosis in ruminants. For example, Reynolds et al., British Pat. No. 2137087A, disclose the use of avoparcin to improve milk production; Raun et al., U.S. Pat. No. 3,928,571 disclose the use of actaplanin, avoparcin (A477), vancomycin and ristocetin to promote growth and to prevent and to treat ketosis; Hamill et al., U.S. Pat. No. 3,952,095, disclose the use of actaplanin to promote qrowth; and Ingle et al., U.S. Pat. No. 4,206,203 disclose use of avoparcin to prevent and to treat ketosis.

New improved antibiotics are continually in demand, particularly for the treatment of human diseases. Increased potency, expanded spectrum of bacterial inhibition, increased in vivo efficacy, and improved pharmaceutical properties, such as greater oral absorption, higher blood or tissue concentrations, longer in vivo half life, and more advantageous rate or route of excretion and rate or pattern of metabolism are some of the goals for improved antibiotics.

In addition to searching for such new compounds in nature, chemical derivatives of existing compounds are being made. An early approach was hydrolysis to remove one or more carbohydrate moieties, (e.g. Chan et al., U.S. Pat. No. 4,521,335). Another approach described in Debono, U.S. Pat. No. 4,497,802 is to acylate the amine terminus of the glycopeptide nucleus.

SUMMARY OF THE INVENTION

In one aspect, the invention comprises new carboxamide derivatives of glycopeptide antibiotics. Representatives of these compounds are Ardacin aglycone-2-hydroxy-ethylamide), Ardacin aglycone-(2-isobutylcarbamoylethylamide) and Ardacin aglycone-(2-N-methylaminoethyl amide).

In yet other aspects, the invention is an antibacterial composition comprising such antibiotics, a method for treating or preventing gram-positive bacterial infections in an animal (including man) by administration of such antibiotics, an animal feed composition comprising such antibiotics to increase propionate production in the rumen or cecum of a meat or milk producing animal, an animal feed premix containing such antibiotics, a method of improving the growth rate of a meat producing animal by administration of such antibiotics, a method of improving the efficiency of feed utilization in a meat or milk producing animal by administration of such antibiotics and a method for improving milk production in a lactating ruminant by administration of such antibiotics.

These and other aspects described herein below are considered embodiments of the same invention and are fully disclosed herein.

DETAILED DESCRIPTION

The antibiotics of this invention are chemically prepared carboxamide derivatives of other glycopeptide antibiotics of the vancomycin/ristocetin class. They are represented by formula I:

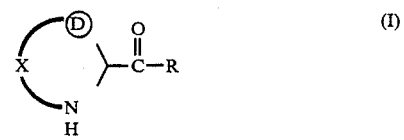

wherein:
X is the remaining portion of a glycopeptide antibiotic of the vancomycin/ristocetin class;
(D) is the D ring of a glycopeptide;
R is $NH_2$ or $NH(CH_2)_n Y$;

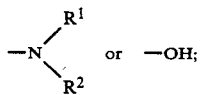

$R^1$ and $R^2$ are independently hydrogen or $C_1$-$C_3$ aklyl;

n is 0 to 6;

and wherein the free carboxyl group of any sugar which is attached to this glycopeptide may also be substituted by R as defined above; or a pharmaceutically acceptable salt thereof.

X can be the remaining portion of any glycopeptide antibiotic of the vancomycin/ristocetin class or chemical derivative thereof which has substantially the core structure found in formula II:

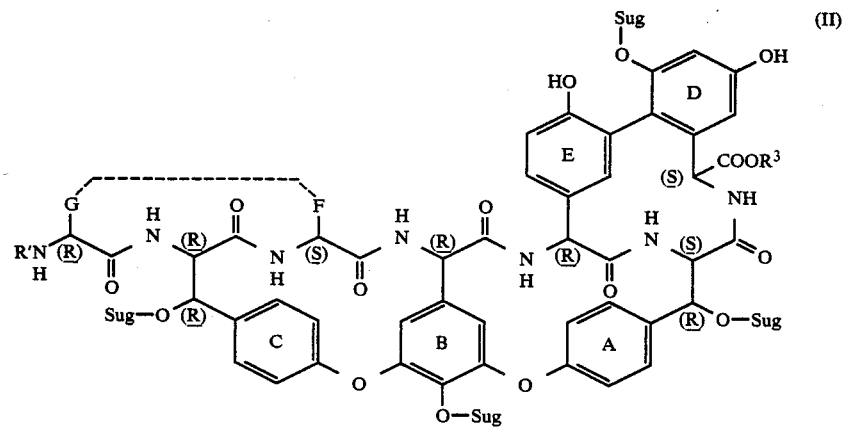

Where:
  Sug is a Carbohydrate or H
  $R^3$ is H or Me
  F is the side chain of asparagine, when G is the side chain of N-methylleucine (i.e., vancomycin); or
  F and G toqether constitute a diphenylether fragment (i.e., ristocetin A, actaplanin A 35512B and teicoplanin); or
  F and G are each an aromatic residue (i.e., actinoidin and avoparcin); or
  G is an oxygenated aromatic residue, when F is the side chain of methionine (i.e., CWI-785 glycopeptides).

Exemplary of glycopeptide antibiotics of the vancomycin/ristocetin class which are included in formula II are vancomycin, ristocetin, actaplanin, A35512B, teicoplanin, AAJ-271 glycopeptides, A41030 factors a, b, c, d. e, f, g, CWI-785 glycopeptides, actinodin, the Ardacins, avoparcin M43A, B, C, D, A51568A and B, AM374, A477, OA7653, AAD-609 glycopeptides (copending application Ser. No. 781,422, now U.S. Pat. No. 4,694,069) and their chemical derivatives.

Chemical derivatives include, e.g., hydrolysis products such as aglycones and pseudoaglycones, and synthetic derivatives such as those disclosed in U.S. Pat. No. 4,497,802 (N-acylglycopeptides), U.S. Pat. No. 4,552,701 [desvancosaminyl and des-(vancosaminyl-O-glucosyl)-glycopeptides]or glycosylated derivations as described in co-pendinq application Ser. No. 948,175, now abandoned.

A preferred subgroup of formula I compounds are those wherein X is the remaining portion of Ardacin aglycone, Ardacin mannosylaglycone, Ardacin A, AAJ-271-$C_1$ and AAJ-271$C_2$, and wherein R is $NH_2$, $NH(CH_2)_2OH$, $NH(CH_2)_2NH_2$, $NH(CH_2)_2NHCH_3$, $NH(CH_2)_2N(CH_3)_2$, $NH(CH_2)_6NH_2$, or $NHNH_2$.

Especially preferred are the compounds in which X is the remaining portion of Ardacin aglycone and R is $NH(CH_2)_2NH_2$, $NH(CH_2)_2OH$, $NH(CH_2)_2N(CH_3)_2$ or $NH(CH_2)_2NHCH_3$. Specific compounds of formula I are:

Ardacin aglycone-(2-hydroxyethyl amide)
Ardacin aglycone-(2-aminoethyl amide)
Ardacin aglycone-(2-N, N-dimethyl aminoethyl amide)
Ardacin aglycone-(2-N-methylaminoethyl amide)
Ardacin mannosylaglycone-(2-aminoethyl amide)
Ardacin mannosylaglycone amide
Ardacin A diamide
Ardacin A-di-(2-hydroxyethyl amide)
Ardacin A-di-(2-aminoethyl amide)
Ardacin aglycone amide
Ardacin aglycone-(6-aminohexyl amide)
AAJ-271$C_1$ diamide
AAJ-271$C_2$ diamide
Ardacin A - dihydrazide The compounds of the invention are prepared in the following manner. The glycopeptide in dry dimethylformamide (DMF) is treated with di-t-butyl dicarbonate and an equivalent amount of triethylamine (TEA) for one hour; the DMF then is removed in vacuo. The residue is treated with ammonium hydroxide in the presence or absence of methanol to effect t-butyl carbonate cleavage. After solvent removal, this N-protected glycopeptide is used without purification in the subsequent step.

A solution of the crude N-protected glycopeptide in dry DMF under nitrogen is cooled to $-10$ to $-15°$ C. (dry ice/ethylene glycol bath). N-Methylmorpholine and isobutyl chloroformate are added and the mixture is stirred for 20 minutes. The amine is added neat or in solution, the cooling bath is removed and the mixture is stirred at room temperature until the reaction is completed. For reactions involving certain alkyl amines, ammonium hydroxide is added subsequently in order to accelerate isobutyl carbonate cleavage. After removal of the solvents, the residue is treated briefly with trifluoroacetic acid (TFA) to effect t-butyl carbamate cleavage and the TFA is removed in vacuo.

The crude product is suspended in aqueous sodium phosphate (0.04 M, pH 7.0) and the pH is adjusted to 8-8.5 with ammonium hydroxide to effect homogeneity. The filtered solution is placed on a column of Affinity gel-10-D-Ala-D-Ala. The column-bound glycopeptide is washed with aqueous sodium phosphate (0.04 and 0.02 M, pH 7.0; one to five column volumes each), water (one to five column volumes), the bound material is eluted with 50% acetonitrile in aqueous ammonium hydroxide (0.1 M) and concentrated.

The affinity-isolated material is purified by semi-preparative reversed-phase HPLC on Whatman Partisil ODS-3 packing in a steel column using an isocratic system of acetonitrile in aqueous potassium phosphate (0.01 M). Like fractions are pooled, diluted to 5–10% organic solvent and loaded onto a column of HP-20 (DIAION) resin. The column-bound product is washed with five to ten column volumes of water prior to elution with 50% aqueous acetonitrile. The acetonitrile is removed in vacuo and the water by lyophilization.

The preferred parent antibiotics used as starting materials in the process of this invention are all members of the group of glycopeptide antibiotics. The AAD-216 antibiotics are described in U.S. Pat. No. 4,548,974. The AAJ-271 antibiotics are described in copending application, Ser. No. 892,027 incorporated by reference herein.

The structure of the AAD-216 and AAJ-271 antibiotics and their carboxamide derivatives are shown in formulas 2a–2s.

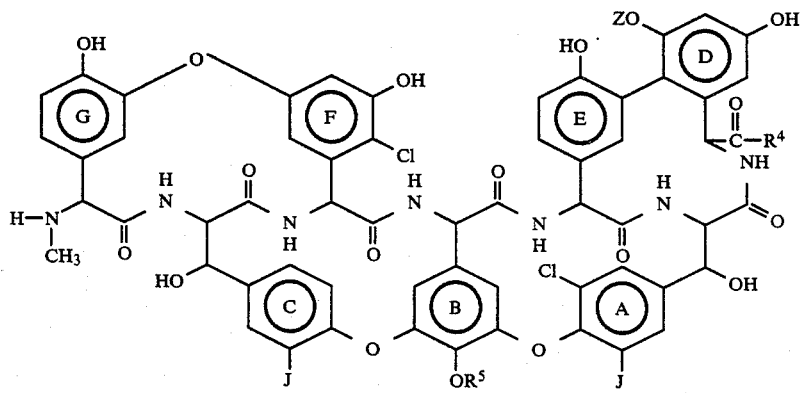

| Compound | | Z | J | R$^4$ | R$^5$ |
|---|---|---|---|---|---|
| 2a | Ardacin aglycone | H | Cl | OH | H |
| 2b | Ardacin mannosylaglycone | D-mannose | Cl | OH | H |
| 2c | Ardacin aglycone amide | H | Cl | NH$_2$ | H |
| 2d | Ardacin aglycone-(2-hydroxyethyl amide) | H | Cl | NH(CH$_2$)$_2$OH | H |
| 2e | Ardacin aglycone-(2-aminoethyl amide) | H | Cl | NH(CH$_2$)$_2$NH$_2$ | H |
| 2f | Ardacin aglycone-(2-N—methylaminoethyl amide) | H | Cl | NH(CH$_2$)$_2$NHCH$_3$ | H |
| 2g | Ardacin aglycone-(2-N,N—dimethylaminoethyl amide) | H | Cl | NH(CH$_2$)$_2$N(CH$_3$)$_2$ | H |
| 2h | Ardacin aglycone-(6-aminohexyl amide) | H | Cl | NH(CH$_2$)$_6$NH$_2$ | H |
| 2i | Ardacin A | D-mannose | Cl | OH | 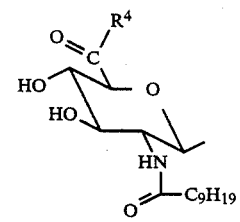 |
| 2j | Ardacin A diamide | D-mannose | Cl | NH$_2$ | " |
| 2k | Ardacin A dihydrazide | D-mannose | Cl | NHNH$_2$ | " |
| 2l | Ardacin A-di-(2-hydroxyethyl amide) | D-mannose | Cl | NH(CH$_2$)$_2$OH | " |
| 2m | Ardacin A-di-(2-aminoethylamide) | D-mannose | Cl | NH(CH$_2$)$_2$NH$_2$ | " |
| 2n | Ardacin mannosylaglycone amide | D-mannose | Cl | NH$_2$ | H |
| 2o | Ardacin mannosylaglycone-(2-aminoethyl amide) | D-mannose | Cl | NH(CH$_2$)$_2$NH$_2$ | H |
| 2p | AAJ-271 C$_1$ | D-mannose | H | OH | 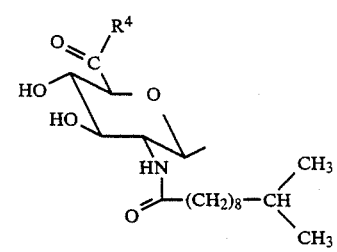 |

| | | | | |
|---|---|---|---|---|
| 2q | AAJ-271 C$_1$ diamide | D-mannose | H | NH$_2$ | 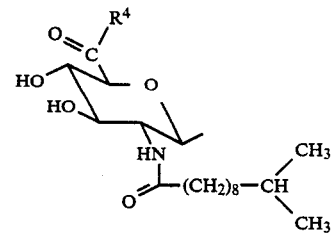 |
| 2r | AAJ-271 C$_2$ | D-mannose | H | OH | 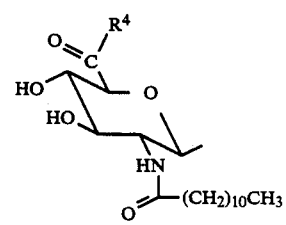 |
| 2s | AAJ-271 C$_2$ diamide | D-mannose | H | NH$_2$ | 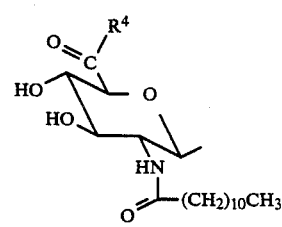 |

The antibiotics of this invention can be converted to physiologically acceptable salts by techniques well-known in the art. Such salts are formed with strong or moderately strong organic or inorganic acids. For example, the antibiotic is reacted with such acid in an aqueous miscible solvent such as ethanol with isolation of the salt by precipitation such as with excess ethyl ether or chloroform with the described salt separating directly or by removing the solvent. Exemplary of salts included in this invention are acetate, oxalate, methane sulfonate, ethane sulfonate, benzene sulfonate, tartrate, citrate, salicylate, acetate, propionate, hydrochloride, hydrobromide, sulfate, toluene-sulfonic, phosphate and nitrate salts.

The antibiotics of this invention, and the salts thereof, all exhibit antibacterial activity in in vitro and in vivo activity assays against gram-positive organisms and can be used, therefore, to prevent or to treat infection in a human or animal by, for example, Staphylococcus (including beta-lactam resistant strains), Streptococcus and Clostridium species.

Representative results of standard microtiter assays are reported in Table 1 which follows, as the minimum inhibitory concentration of antibiotic (mg/ml).

In Table 1, test organisms 1–5 were different strains of Staphylococcus aureus; 6, 8, 11, 13 and 14 were different strains of Staphylococcus epidermidis; 7 was a Staphylococcus haemolyticus; 9 and 10 were different strains of Streptococcus faecalis; and 12 was a Staphylococcus saprophyticus.

TABLE 1

| Compound | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 2c | 0.2 | 0.2 | 0.4 | 0.4 | 0.2 | 0.4 | 0.8 | 0.4 | 0.2 | 0.4 | 0.4 | 0.2 | 0.4 | 0.2 |
| 2d | 0.05 | 0.05 | 0.05 | 0.2 | 0.2 | 0.4 | 0.8 | — | 0.2 | — | 0.8 | 0.4 | 0.2 | 0.4 |
| 2e | 0.05 | 0.05 | 0.05 | 0.2 | 0.05 | 0.1 | 0.05 | 0.1 | 0.05 | 0.1 | 0.1 | 0.05 | 0.05 | 0.05 |
| 2g | 0.2 | 0.1 | 0.2 | 0.4 | 0.1 | 0.2 | 0.2 | 0.2 | 0.1 | 0.2 | 0.2 | 0.1 | 0.05 | 0.05 |
| 2f | 0.2 | 0.2 | 0.1 | 0.2 | 0.1 | 0.2 | 0.2 | 0.1 | 0.1 | 0.1 | 0.1 | 0.1 | 0.05 | 0.1 |
| 2h | 0.1 | 0.1 | 0.4 | 0.1 | 0.1 | 0.1 | 0.2 | 0.1 | 0.1 | 0.1 | 0.2 | 0.2 | 0.1 | — |
| 2n | 0.2 | 0.8 | 0.1 | 3.1 | 0.4 | 1.6 | 1.6 | — | 0.2 | — | 6.3 | 1.6 | 1.6 | 1.6 |
| 2o | 0.4 | 0.4 | 0.4 | 0.4 | 0.4 | 0.4 | 1.6 | 0.8 | 0.2 | 0.2 | 0.8 | 0.4 | 0.1 | — |
| 2j | 0.8 | 1.6 | 0.8 | 3.1 | 1.6 | 6.3 | 3.1 | 6.3 | 0.2 | 0.1 | 6.3 | 3.1 | 3.1 | 0.8 |
| 2k | 3.1 | 3.1 | 1.6 | 6.3 | 3.1 | 12.5 | 12.5 | 12.5 | 0.4 | 0.1 | 12.5 | 6.3 | 3.1 | 3.1 |
| 2l | 0.2 | 0.2 | 0.2 | 0.4 | 0.4 | 1.6 | 0.8 | 0.4 | 0.1 | 0.1 | 0.8 | 0.8 | 0.2 | — |
| 2m | 0.1 | 0.1 | 0.1 | 0.8 | 0.4 | 1.6 | 0.8 | 0.1 | 0.1 | 0.1 | 0.1 | 0.8 | 0.4 | 0.2 | — |
| 2q | 0.8 | 1.6 | 0.8 | >1.6 | 1.6 | 12.5 | 3.1 | 6.3 | 0.2 | 0.2 | 12.5 | 12.5 | 3.1 | 3.1 |
| 2s | 50 | — | — | 25 | 25 | 50 | 12.5 | 50 | 3.1 | 6.3 | — | — | — | — |
| Vancomycin | 3.1 | 1.6 | 1.6 | >3.1 | 1.6 | 3.1 | 3.1 | 3.1 | 3.1 | 3.1 | 3.1 | 3.1 | 3.1 | 3.1 |
| 2a | 0.8 | 0.8 | 0.4 | 0.4 | 0.8 | 6.3 | 3.1 | 0.8 | 0.8 | 1.6 | 1.6 | 1.8 | 0.8 |
| 2b | 1.6 | 1.6 | 0.8 | >1.6 | 1.6 | 12.5 | 25 | 6.3 | 0.8 | 0.8 | 25 | 3.1 | 6.3 | — |
| 2i | 6.3 | 3.1 | 0.8 | >6.3 | 3.1 | 50 | 25 | 25 | 0.8 | 0.8 | 25 | 12.5 | 6.3 | 5.1 |
| 2p | 0.4 | 0.4 | 0.2 | 0.8 | 0.4 | 6.3 | 6.3 | 25 | 6.3 | 6.3 | 25 | 1.6 | 6.3 | 6.3 |
| 2r | 0.8 | 0.8 | 0.2 | 1.6 | 0.8 | 25 | 12.5 | 12.5 | 0.2 | 0.2 | 25 | 1.6 | 6.3 | 3.1 |

The invention includes within its scope pharmaceutical compositions containing at least one of the abovementioned antibiotic compounds and a pharmaceutically acceptable carrier. The compositions may also contain other active antibacterial agents or may be a mixture of compounds of this invention. The compositions may be made up in any pharmaceutical form appropriate for the route of administration in question. Such compositions are exemplified by solid compositions for oral administration, such as tablets, capsules, pills, powders and granules; liquid compositions for oral administration such as solutions, suspensions, syrups and elixirs; preparations for parenteral administration such as sterile solutions, suspensions or emulsions; and preparations for topicaladministration such as gels, creams, ointments or salves.

Effective injectable compositions containing the compounds of this invention may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants may be necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and suqars can be useful suspending agents.

For use as an antibacterial agent, the compositions are administered so that the concentration of the active ingredient is qreater than the minimum inhibitory concentration for the particular organism treated. The antibiotic compounds of the invention are effective in preventing and treating infection in an animal, including a human, by gram-positive pathogenic bacteria. A typical parenteral dosage such as by intramuscular injections, for a 70 kg human, is about 100 to about 2000 mg, preferably about 500 to about 1000 mg, per day, althouqh the optimum dosage will, of course, depend on factors such as the nature and severity of the bacterial infection, the age and weight of the animal and the route of administration. Optimum dosages can be determined readily by use of standard techniques. Once a day administration is preferred, though bid and tid administration is possible.

Certain antibiotics of this invention were also shown to have activity as animal growth promotants and as animal feed utilization efficiency enhancers. For increasing feed-utilization efficiency and promoting growth, a compound of this application is administered orally in a suitable feed in an amount of from about 1 to about 200 grams per ton of total feed. For enhancing milk production in ruminants, oral administration of a daily amount of from about 0.1 to about 10 mg/kg of body weight is suggested.

The animal feed compositions of this invention comprise the normal feed rations of the meat and milk producing animals supplemented by a quantity of an active ingredient selected from among the antibiotics of formula I, and their salts, or a mixture thereof which is effective for improving the growth rate and feed efficiency of the animals but which is not toxic or noxious to a degree that the animals will reduce ingestion of the ration. The quantity of the active ingredient will vary, as is known to the art, with factors such as the cost of the ingredient, the species and the size of animal, the relative activity of the antibiotic selected or the type of feed ration used as the basal feed.

Representative feed rations for swine and poultry are as follows:

A swine ration for growing hogs of 40–100 pounds body weight is prepared using the following formula:

| Corn, ground | 78.15% |
|---|---|
| Soybean oil meal, 44% | 17.0% |
| Meat scraps, 50% | 3.0% |
| Oyster shell flavor | 0.4% |
| Bone meal | 0.5% |
| Zinc oxide | 0.1% |
| Vitamin A, B, $B_{12}$ & D supplement | optional |

A chicken ration for broilers is prepared using the following formula:

| Yellow corn meal | 67.35% |
|---|---|
| Soybean oil meal | 24.00% |
| Menhaden fish meal | 6.00% |
| Steamed bone meal | 1.00% |
| Ground limestone | 1.00% |
| Iodized salt | 0.34% |
| 25% choline chloride | 0.13% |
| Vitamin $B_{12}$ | 0.10% |
| Maganese sulfate | 0.02% |
| Vitamin mix | 0.06% |

Swine feed from weanling to fattening or finishing rations may be supplemented. Swine eat from about 2 lb. of ratio per day (for a 25 lb. pig) to 9 lb. per day (for a 150 lb. pig). Most rations are comprised of a corn base supplemented with legume silage, wheat bran, oats, barley, molasses or a protein supplement.

Poultry feeds comprise starter rations, broiler rations and laying rations. The rations are usually based on ground corn, corn meal or soybean meal. The broiler rations often contain high energy supplements such as added fats, proteins and vitamins. Turkey rations are similar, but comprise only a starting ration and a growing ration. Chickens or pheasants eat from 0 03–0.3 lbs. of feed per day, turkeys twice that much. Estimated intake of feed is dependent on the weight and age of the meat producing animal.

The active ingredients selected from among the antibiotics of formula I or a mixture thereof are mixed uniformly with such feed rations to give supplemented rations which are then fed as to custom, which is, most often, ad libitum. Conveniently, to do this, a premix of the supplemental growth promotant of this invention, optionally combined with or without other supplements known to this art such as an anthelmintic, a nitrogen source or an antibiotic, for example, virginiamycin or oxytetracycline is prepared by the manufacturer for sale to the formulators or feed lot operators. The concentration of the active ingredients selected from among the antibiotics of formula I or a mixture thereof in the premix is usually from 5–75% by weight or a concentration 100–2000 times greater than that in the complete feed ration The premix form may be liquid or solid. Premix vehicles are corn oil, cottonseed oil, molasses or distillers solubles to form a liquid premix preparation. Sucrose, lactose, corn meal, ground corn, flour, calcium carbonate or soybean meal are often used as bases for solid premix preparations. The premix composition is, then, mixed uniformly with whole ration which is fed to the target animal. Such premix compositions are included in the term "feed compositions" as used herein.

The concentration of the active ingredients selected from among the antibiotics of formula I or a mixture thereof in the complete ration is a nontoxic but active quantity chosen, for example, from a range of about 1–1000 parts of active ingredient by weight per million parts of whole feed (ppm) or about 2–115 grams per ton. Advantageously, a nontoxic quantity of active ingredient is chosen from the range of 10–50 ppm.

The method of this invention comprises feeding to monogastric or ruminant, meat or milk producing animals, especially beef and dairy cattle, sheep, swine and poultry, an effective growth promoting but nontoxic quantity of an active ingredient selected from among the antibiotics of formula I. Other monogastric animals whose digestive tract also features fermentation in a cecum or cecum-like chamber are rabbits and horses.

The supplemented feed rations, described above, are presented in the animal by methods known to the art. Ad libitum feeding in the pasture, pen or growing shed is most convenient to increase the growth and milking rate of the animal and to increase the feed efficiency of the operation.

The following examples are illustrative, and not limiting of this invention.

Example 1

Preparation of N-t-BOC Ardacin aglycone 800 mg (616 umoles) of Ardacin aglycone in 20 ml of dry dimethylforamide (DMF) was treated with 570 ul (2.47 nmoles, 4 eq) of di-t-butyl dicarbonate and 345 ul (2.47 nmoles, 4 eq) of triethylamine (TEA for one hour. The DMF was then removed in vacuo. The residue was treated with 7.5 ml of 7.5 N ammonium hydroxide in the presence of 7.5 ml methanol for 3 hours to effect t-butyl carbonate cleavage. After removal of the solvent, the N-t-BOC-Ardacin aglycone was used without purification in subsequent steps.

Example 2

Preparation of Ardacin aglycone - (2-aminoethyl amide)

A solution of 81 mg (58 u moles) of crude N-t-BOC Ardacin aglycone in 3 ml of dry DMF under nitrogen is cooled to −10° to −15° C. (dry ice/ethylene glycol bath). 300 uL (2.7 umoles 47 eq) of isobutyl chloroformate was added and the mixture was stirred for 20 minutes. 3.5 ml of ethylene diamine (3.5 ml, 52 mmoles) was added, the cooling bath removed, and the mixture was stirred at room temperature for 2 hours. After removal of the solvents, the residue was treated for 15 minutes with 5 ml of trifluoroacetic acid (TFA) to effect t-butyl carbamate cleavage and the TFA was removed in vacuo.

The crude product was suspended in 250 ml of 0.04 m sodium phosphate pH 7.0. The pH was adjusted to 8–8.5 with ammonium hydioxide to effect homogenity. The filtered solution was placed on a column of 10-D-Ala-D-Ala affinity gel, washed with 0.04 M and 0.02 M sodium phosphate (pH 7.0) and water and then eluted with 50% acetonitrile in aqueous ammonium hydroxide (0.1 M) and concentrated.

The affinity-isolated material was purified by semi-preparative reversed-phase HPLC on Whatman Partisil® ODS-3 packing in a steel column using an isochratic system of acetonitrile in aqueous potassium phosphate (0.01 M). Like fractions were pooled, diluted to 5–10% organic solvent and loaded onto a Magnum 20 column. The column-bound product was eluted with 20% acetonitrile in 0.01 M $KH_2PO_4$ pH 3.2 at 25 ml per minute. The acetonitrile was removed in vacuo and the water by lyophilization to give 19 mg of Ardacin aglycone (2-aminoethyl amide) (24% yield).

HPLC was conducted on a Beckman 345 Binary Liquid Chromatograph using a linear gradient of acetonitrile in monobasic potassium phosphate (0.01 M, pH 3.2) at a flowrate of 1.5 ml/min with spectrophotometric detection at 220 nm. The column was an Altex Ultrasphere-ODS (4.6×150 mm) with a brownlee Spheri-5 RP18 precolumn (1.6×30 mm, 5 mm). The linear qradient was 14–37% acetonitrile over 8 min.

Mass spectral data was obtained using a VG ZAB-1F-HF mass spectrometer equipped with a standard FAB source in a matrix of monothiolglycerol containing oxalic acid.

Examples 3–15

Using substantially the procedures of both Examples 1 and 2, the compounds of Examples 3–15 were obtained by using the appropriate glycopeptide and amine starting materials. Yields and analytical data are given in Table 2.

TABLE 2

| Example No. | Compound | yield | Low Resolution FAB MS MH+ | $E_{1\%}$ | pI |
|---|---|---|---|---|---|
| 3 | Ardacin aglycone amide | 70% | 1295 | 73 | 7.1 |
| 4 | Ardacin aglycone-(2-hydroxyethyl amide) | 99% | 1339 | 67 | 7.1 |
| 5 | Ardacin aglycone-(2-N—methylaminoethyl amide) | 30% | 1352 | 70 | 7.7 |
| 6 | Ardacin aglycone-(2-N,N—dimethylaminoethyl amide) | 48.5% | 1366 | 72 | 7.7 |
| 7 | Ardacin aglycone-(6-aminohexyl amide) | 28% | 1394 | 71 | 7.7 |
| 8 | Ardacin A diamide | 32% | 1785 | 43 | 7.2 |
| 9 | Ardacin A dihydrazide | 20.5% | 1815 | 49 | 7.0 |
| 10 | Ardacin A-di-(2-hydroxyethyl amide) | 74% | 1873 | 56 | 7.3 |
| 11 | Ardacin A-di-(2-aminoethyl amide) | 39% | 1871 | 51 | 8.4 |

TABLE 2-continued

| Example No. | Compound | yield | Low Resolution FAB MS MH+ | $E_{1\%}$ | pI |
|---|---|---|---|---|---|
| 12 | Ardacin mannosylaglycone amide | 100% | 1457 | 72 | 7.1 |
| 13 | Ardacin mannosylaglycone (2-aminoethyl amide) | 75.3% | 1500 | 64 | 7.8 |
| 14 | AAJ-271 $C_1$ diamide | 33.7% | 1729 | 52 | 7.3 |
| 15 | AAJ-271 $C_2$ diamide | 47.8% | — | 62 | — |

1 Examples 16–26

Using substantially the procedures of both Examples 1 and 2, the compounds of Examples 16–26 may be prepared by using the appropriate glycopeptide and amine starting materials.

| Example No. | Compound |
|---|---|
| 16 | vancomycin aglycone amide |
| 17 | teicoplanin aglycone amide |
| 18 | A41030 a amide |
| 19 | CWI-785 aglycone amide |
| 20 | AM 374 amide |
| 21 | AAD-609 aglycone amide |
| 22 | actinoidin aglycone amide |
| 23 | A 477 aglycone amide |
| 24 | OA 7653 aglycone amide |
| 25 | avoparcin aglycone amide |
| 26 | O-(B-D—glucopyranosyl)-HPB-4" amide |

I claim:
1. A compound of the formula:

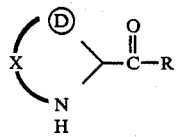

wherein
X is the remaining portion of an Ardacin glcopeptide antibiotic or a hydrolysis product, N-acyl or glycosylated derivative thereof;
(D) is the D ring of Ardacin
R is $NH_2$ or $NH(CH_2)_nY$;
Y is

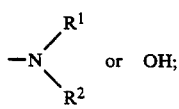

$R^1$ and $R^2$ are independently hydrogen or $C_1$–$C_3$ alkyl;
n is 0 to 6;
and wherein the free carboxyl group of any sugar which is attached to the glycopeptide antiobitic may also be substituted by R as defined above; or a pharmaceutically acceptable salt thereof.

2. A compound of claim 1 wherein X is the remaining portion of: Ardacin aglycone, Ardacin mannosylaglycone, or Ardacin A.

3. A compound o claim 1 wherein R is: $NH_2$, $NH(CH_2)_2OH$, $NH(CH_2)_2NH_2$, $NH(CH_2)_2NHCH_3$, $NH(CH_2)_2N(CH_3)_2$, $NH(CH_2)_6NH_2$, or $NHNH_2$.

4. A compound of claim 3 wherein R is selected from a group consisting of $NH(CH_2)_2NH_2$, $NH(CH_2)_2OH$, $NH(CH_2)_2N(CH_3)_2$ or $NH(CH_2)_2NHCH_3$.

5. A compound of claim 4 which is Ardacin aglycone-(2-aminoethylamide).

6. A compound of claim 4 which is Ardacin aglycone-(2-hydroxyethyl amide).

7. A compound of claim 4 which is Ardacin aglycone-(2-N,N-dimethylaminoethyl amide).

8. A compound of claim 4 which is Ardacin aglycone (2-N-methylaminoethyl amide).

9. A compound of claim 1 selected from the group consisting of:
Ardacin aglycone amide
Ardacin aglycone-(6-aminohexyl amide)
Ardacin A-diamide
Ardacin A-dihydrazide
Ardacin A-di-(2-hydroxyethyl amide)
Ardacin A-di-(2-aminoethyl amide)
Ardacin mannosylaglycone amide
Ardacin mannosylaglycone-(2-aminoethyl amide).

10. A pharmaceutical composition for treating gram-positive bacterial infections in an animal which comprises an effective amount of a compound of claim 1, and a pharmaceutically acceptable carrier therefor.

11. A pharmaceutical composition for treating gram-positive bacterial infections in an animal which comprises an effective amount of a compound of claim 5, and a pharmaceutically acceptable carrier therefor.

12. A pharmaceutical composition for treating gram-positive bacterial infections in an animal which comprises an effective amount of a compound of claim 6, and a pharmaceutically acceptable carrier therefor.

13. A method of treating susceptible gram-positive bacterial infections which comprises administering an effective amount of a composition of claim 10 to an infected or susceptible animal.

14. A method of treating susceptible gram-positive bacterial infections which comprises administering an effective amount of a composition of claim 11 to an infected or susceptible animal.

15. A method of treating susceptible gram-positive bacterial infections which comprises administering an effective amount of a composition of claim 12 to an infected or susceptible animal.

16. A feed composition for increasing feed-utilization efficiency in non-human animals or for increasing propionate production in ruminants which comprises an effective amount of a compound of claim 1, or a pharmaceutically-acceptable salt thereof, and a standard feed ration.

17. A method for increasing feed-utilization in an animal which comprises orally administering to the animal an effective amount of composition of claim 16 to the animal.

18. A method of improving milk production in lactating ruminants comprising orally administering to the ruminant an effective amount of a composition of claim 16.

* * * * *